United States Patent [19]

Latypov et al.

[11] 4,112,935
[45] Sep. 12, 1978

[54] APPARATUS FOR SURGICAL TREATMENT OF SCOLIOSIS

[76] Inventors: Anvar Latypovich Latypov, ulitsa Shmidta, 37, kv. 33; Vakif Barievich Abrarov, ulitsa Polevaya, 32, kv. 4, both of Kazan, U.S.S.R.

[21] Appl. No.: 738,467

[22] Filed: Nov. 3, 1976

[51] Int. Cl.² .............................................. A61F 5/01
[52] U.S. Cl. ...................................... 128/69; 128/75; 128/78
[58] Field of Search ................. 128/7.5, 78, 69, 92 R, 128/92 A

[56] References Cited

U.S. PATENT DOCUMENTS 3,926,182  12/1975  Stabholz ................................. 128/75

FOREIGN PATENT DOCUMENTS 257,376  3/1912  Fed. Rep. of Germany ............. 128/78
622,315  3/1934  Fed. Rep. of Germany ............. 128/78

Primary Examiner—Robert W. Michell
Assistant Examiner—Michael H. Thaler
Attorney, Agent, or Firm—Steinberg & Blake

[57] ABSTRACT

An apparatus for surgical treatment of scoliosis, comprising a framework formed by parallel struts secured at their ends by yokes and fixed on the patient's body by means of a system of belts, connected with the framework by stay rods fastened to the struts. Flexible braces serve for exerting a corrective force on the vertebrae, whose one ends are intended for attachment to the vertebrae, and the other ends are attached to mechanisms for the dosed tension of the flexible braces, secured on the struts and movable therealong.

12 Claims, 16 Drawing Figures

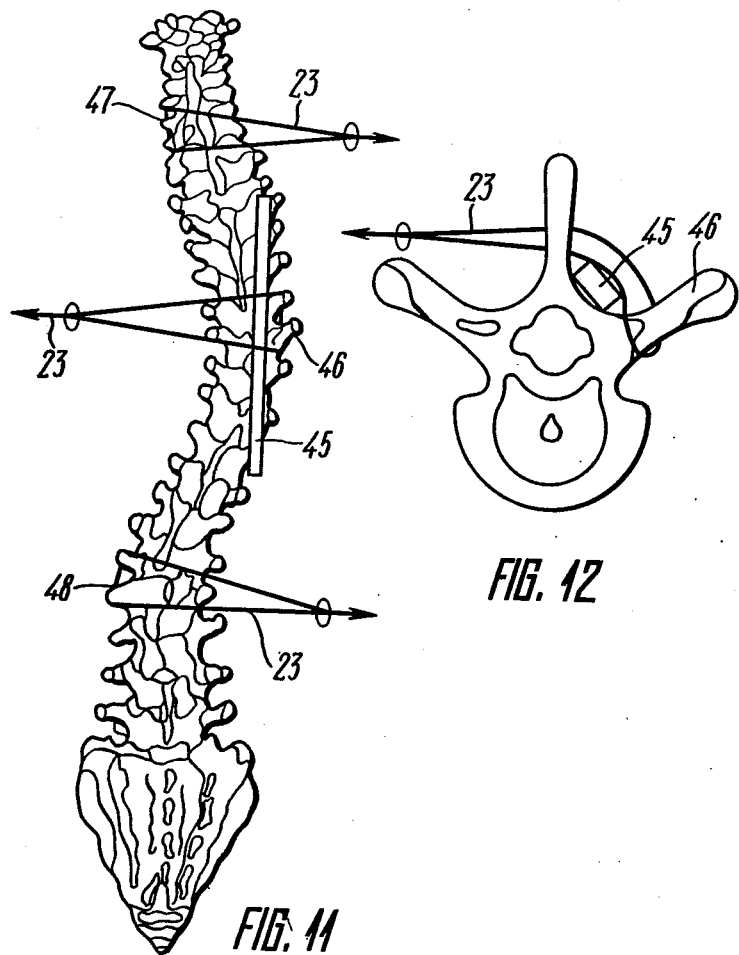

APPARATUS FOR SURGICAL TREATMENT OF SCOLIOSIS

This invention relates to medicine, and more particularly to devices for corrective and stabilizing treatment of scolioses.

The present invention may be used for preliminary correction of scoliosis with subsequent osteoplastic fixation of the spinal column, or for correction and stabilization of scoliosis simultaneously. The latter can be achieved by the method of posterior spondylodesis, wedge-like resection of the vertebral bodies on the convex side, and by diskectomy.

Known in the art is a great number of surgical methods, devices and apparatus for the correction of scoliosis.

The better known, which have received greater or lesser practical application, are the following.

There exists a "jack-type" device known as a distractor. This distractor comprises two metal rods, one end of each rod being bifurcated at a 30° angle, while the other end is threaded. Both rods are interconnected by a sleeve, a cylindrical tube with a two-way thread.

With its bifurcated ends, the distractor is mounted on the bases of the transverse processes of the vertebrae at the base of the scoliotic arch, and its sleeve is then unscrewed to the maximum. At the same time, posterior spondylodesis is performed.

This distractor, however, has a corrective force of low efficiency, which is applied to the spinal column during surgery and cannot be altered throughout the period of the distractor's application. Besides, the use of this distractor may cause complications as a result of fracturing the transverse processes of the vertebrae and patients are bed-ridden for a long time. The removal of the distractor requires a second surgical operation, no less traumatic than the first.

Also known in the art is a similar method of correcting scoliosis with the aid of a metal distractor and contractor. The contractor comrises two metal rods with bent ends, the straight ends of the rods being linked by a threaded sleeve, and the bent ends being affixed to the transverse processes of the vertebrae on the convex side of the scoliotic arch. Upon the rotation of the sleeve, the contractor pulls at the transverse processes, thereby correcting the curvature of the spinal column. The distractor, likewise, comprises two metal rods whose ends are connected through a threaded sleeve. The other ends of the rods are bifurcated. The distractor is mounted on the concave side of the spinal column's curvature with its bifurcated ends pressing against the transverse processes of the vertebrae. The unwinding of the sleeve extends the distractor, thereby correcting the curvature of the spinal column.

This method offers certain advantages over the former, due to the dual corrective force. However, the contractor and distractor permit correction of the curvature of the spinal column only during surgery, and prevent subsequent enhancement of the correction. The danger of fracturing the transverse processes of the vertebrae also remains. Patients are bedridden for long and the removal of the mechanisms requires a repetition of surgery.

Also known in the art of treating scoliosis is the use of a steel spring, whose hook-like ends are fixed on the transverse processes of the vertebrae on the convex side of the scoliotic curvature, with the spring extended. The spring acts as a contractor for a longer period of time, which distinguishes it from the previously described constructions, but their other disadvantages are found here too. These are the hazard of fracturing the transverse processes, the patients being bed-ridden for long, inadequate correction, and the need for a second surgical operation to remove the spring.

There is also known an apparatus for the skeletal traction of the spinal column in scoliosis. This apparatus is formed by two rings, the head and the pelvic ones, interconnected by four expansion stay rods. When applying the apparatus, two metal pins are drawn through the iliac bones of the pelvis, their ends being secured on the pelvic ring. Four metal pins are inserted into the bones of the cranium and affixed to the head ring. By gradually unwinding the sleeves of the expansion stay rods between the pelvic and head rings, longitudinal traction of the spinal column by the pelvic bone and the bones of the cranium is effected.

The longitudinal traction of scoliosis, however, produces a low corrective effect. In cases of thoracic and lumbar scolioses, such traction produces a greater traumatic effect on the cervical region of the spinal column with its weak ligamentous apparatus, than a corrective one on the curvation of the thoracic and lumbar regions. Nor are neurological disorders ruled out as a result of traumatizing the nervous roots of the cervical region of the spinal cord. Hazardous, again, is the introduction of metal pins into the cranial bones in childhood, when their formation is not complete yet. Besides, the rings surrounding the head and pelvis prevent the patient from usng an ordinary bed, as a special device is required, and this makes the use of the apparatus much more complicated.

Thus, the main drawbacks of this apparatus are the danger of possible grave neurological complications, inadequate corrective effect, difficulty in using it and complicated bed-care.

Also used for scoliosis is an apparatus for the skeletal traction of the spinal column, comprising a head ring (halo) with four threaded pins which are also inserted into the cranial bones with their outer ends fixed on the head ring. The upper ends of three metal expansion stay rods are affixed to the head ring, while the lower ends are embedded in a plaster-of-Paris jacket. The stay rods are gradually extended by means of expansion sleeves, thereby effecting the traction of the spinal column.

The disadvantages of this apparatus are the same as in the previous construction.

Still another prior art apparatus to be used for external skeletal traction of the spinal column comprises a supporting shaft at the ends of which two L-shaped end feet are affixed at a right angle thereto, with disc rests on the tips. A third foot, also L-shaped and with a disc rest on the tip, is affixed to the middle of the shaft set in a direction opposite to that of the end feet.

The apparatus is mounted on the patients's back alongside the spinal column so that all the three disc rests rest upon the patient's back without any additional fixation.

Nylon threads attached to the spinous processes of three vertebrae, at the apex of the curvature and at its two bases, are brought out through the soft tissues and the skin of the back, and each of them is secured on the appropriate foot of the apparatus and tightened. In this manner, the scoliotic curvature is drawn from its apex towards the concave side and from the extreme vertebrae, towards the convex side. The operating principle of the apparatus provides for corrective skeletal traction of the spinal column perpendicularly to its longitudinal axis and in opposite directions, which should be regarded as an advantage over the other above described constructions. However, it has a number of serious drawbacks as well. The apparatus is not fixed to the patients's trunk, but rests on 3 feet on the skin of the back, which fails to ensure its stability. The protracted use of the apparatus may result in the appearance of skin sores under the disc rests of the feet. The apparatus prevents the patient from rising, forcing him to lie constantly in the prone position. The corrective force is not continuous, but is an extension per contiguitatem, non-dosed. Therefore, physiological principles are lacking and the effect in treating scoliosis is poor.

Also known is an apparatus for the surgical treatment of scoliosis comprising a supporting frame formed by a guide plate, the latter formed by two parallel guiding elements and placed on the patient's back along the spinal column, and by two U-shaped struts affixed to the ends of the guide plate and fitted at the ends with supports resting on the patient's back and serving to secure the frame to his trunk with straps. The means of exerting correcting forces on the vertebrae appear as two end stops and one middle stop, each of them formed by two rods, a straight and a bent one, serving to clamp, like stirrups, the transverse processes of the patient's vertebrae. The two end stops can glide along the guide plate, while the middle stop is fastened to the middle part of the guide plate by means of a transverse motion mechanism ensuring the movement of the middle stop in a direction perpendicular to the guide plate. The middle stop is connected with the end ones by means of spring-loaded telescopic bushes. Rotation of the screw of the transverse motion mechanism brings the middle stop closer to the guide plate and moves the two end stops connected with the middle stop farther apart.

When applying the apparatus, the two end stops are fastened on the spinous processes of the two vertebrae situated at the base of the scoliotic arch by piercing the skin and the thoracolumbar fascia. The middle stop is fastened in the same manner to the spinous process of the vertebra situated at the apex of the scoliotic arch. The apparatus is secured on the patient's back with straps.

The correction of the scoliotic arch is effected by rotating the screw of the transverse motion mechanism and, simultaneously, the end stops, moving along the axis of the spinal column, effect the longitudinal traction of the curvated column. This traction procedure is repeated from time to time. This apparatus is based also on the principle of skeletal vertebral traction, while carrying out lateral and longitudinal extension simultaneously.

However, the weakness of the spinous processes in child patients and the small area of contact between the metal stops of the apparatus and the spinous process of an individual vertebra preclude the application of forces necessary for scoliotic correction because of the danger of fractioning the bone elements of the vertebra. The apparatus involves keeping the patient bed-ridden in the prone position for a long time. The stops protruding through the skin must of necessity be quite massive and, therefore, keep skin wounds open with the ever present danger of infection. Nor does the apparatus allow to control the corrective force. The apparatus is recommended for use in order to effect the preliminary stage of scoliotic redressment, whereas the main stage, that of spondylodesis, requires a second surgical operation and further prolongation of treatment.

It is an object of the present invention to provide an apparatus for the surgical treatment of scoliosis that will allow to carry out effective correction of scoliosis and spondylodesis at the same time.

Another object of the invention is to provide an apparatus for the surgical treatment of scoliosis that will allow the patient to get out of bed, to sit and to walk, throughout the entire period of treatment.

Still another object of the invention is to provide an apparatus that will make it possible to avoid hazardous complications and a repetition of the surgical operation.

These objects are achieved in that, in an apparatus for the surgical treatment of scoliosis, which is essentially a supporting framework fastened to the patient's body through a system of belts, and mounted on which are means for exerting a corrective force on the vertebrae, to be attached to the curvated portions of the spinal column in accordance with the invention, the framework is formed by at least two parallel struts linked together at their ends through two yokes and fastened by means of adjustable stay rods to the belts so that, when applying the apparatus, the struts are situated along both sides of the patient's trunk approximately in the plane of the spinal column, and the means for exerting the correcting force appear as flexible braces, whose one ends are intended to be fastened on the vertebrae, with their other ends fastened to mechanisms for the dosed tension of the flexible braces, set on the struts and movable therealong.

Attached to the patients's trunk, the apparatus makes it possible for the patient to walk, sit and lie without interfering with the process of treatment. This is an important advantage in that it provides better conditions for breathing, and for the functioning of the cardio-vascular system, the muscles and other organs. Besides, bed-care procedures are much easier.

The patient can perform all the natural bodily functions practically unassisted throughout the entire period of treatment.

Owing to the use of flexible braces fastened to the vertebrae at several points and acting upon the spinal column in opposite directions, the apparatus allows to carry out the effective correction of scoliosis. During this process, the mechanisms for dosing the tension of the flexible braces allow to adjust and control the corrective forces applied to the spinal column.

When fastening the flexible braces to the vertebrae, an autoplastic bone graft is placed on the main curvation of the spiral column, thereby ensuring, at the same time, a posterior spondylodesis and the correction of scoliosis. This excludes injury to the bone elements of the spinal column to which the flexible braces are fastened.

The removal of the apparatus does not require a repetition of surgery.

The apparatus may be fitted with two pairs of struts, to one pair of which, situated along both sides of the patient's trunk approximately in the plane of the spinal column, stay rods are affixed, and the other pair, placed somewhat further along the yokes towards their tips, serves for carrying the mechanisms fo the dosed tension of the flexible braces.

This allows to arrange the tension dosing mechanisms so as to ensure the necessary position of the flexible braces acting upon the spinal column in pre-set directions while excluding the cutting of the patient's skin by the flexible braces or the formation of skin sores.

It is advisable that each yoke of the apparatus be made of two halves interconnected through a threaded sleeve to ensure the adjustment of the distance between the struts secured in the yokes. This allows to alter the overall dimensions of the apparatus according to the individual size of the patient's body.

It is desirable that the stay rods be secured in the struts, so as to be movable therealong and rotatable at the points of their connection to the struts and belts, thereby making it easy to adjust the apparatus to the patient's trunk.

It is advisable that the struts be secured in the yokes so as to be movable along the latter, for adjusting the distance between the struts.

The mechanisms for the dosed tension of the flexible braces may be made with rack-and-pinions, connected to spring dynamometers, and fitted with ratchet catch pawls, which makes it possible to set or relieve the required corrective force on every one of them independently of the other.

It is desirable that the struts of the apparatus be secured in at least one of the yokes so that they are movable longitudinally, making it possible to adjust the distance between the yokes.

The proposed apparatus is simple in design and is easily disassembled for compact packing and transportation.

The invention will now be described in greater detail with reference to preferred embodiments thereof, taken in conjunction with the accompanying drawings, wherein:

FIG. 11 shows the fastening of the flexible braces of the apparatus to the patient's spinal column, in accordance with the invention;

FIG. 12 shows the fastening of a flexible brace of the apparatus to a transverse process of a vertebra;

Figure 1:
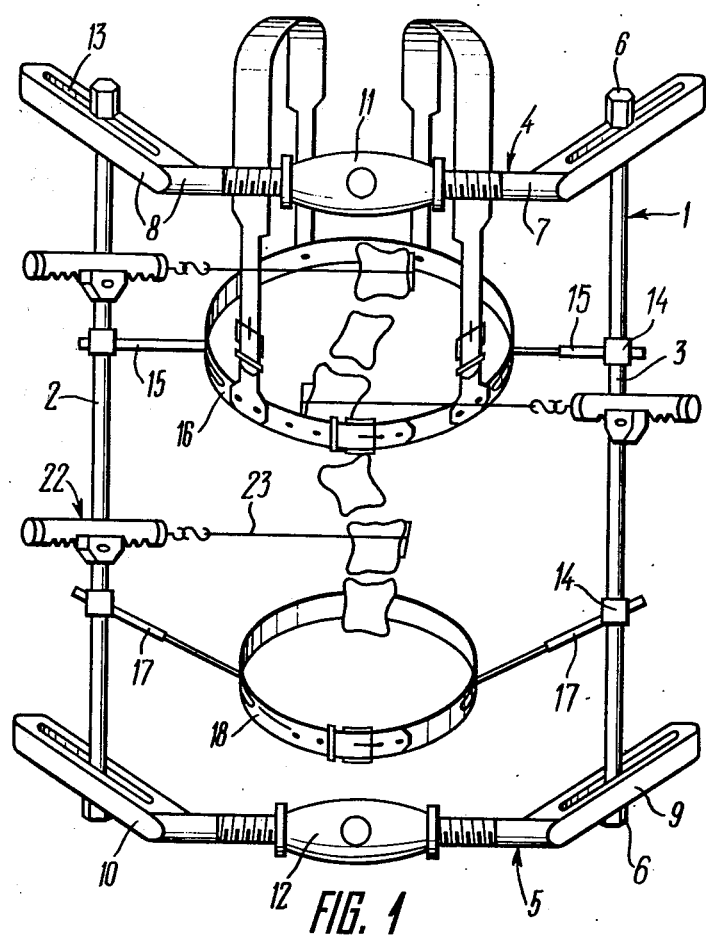
FIG. 1 shows an apparatus for the surgical treatment of scoliosis with one pair of struts, in accordance with the invention.

Referring now to FIG. 1, an apparatus for the surgical treatment of scoliosis comprises a supporting frame means 1 including a strut means formed, in the embodiment of FIG. 1, by two parallel struts 2 and 3 movably connected at their ends, which are threaded, by means of yokes 4 and 5 in which they are secured with nuts 6.

Such a connection of the yokes 4 and 5 with the struts 2 and 3 makes it possible to change the position of the yokes 4 and 5 longitudinally relative to the struts 2 and 3, by adjusting the distance between the yokes 4 and 5.

The yoke 4 is made up of two halves 7 and 8, while the yoke 5 is made up of two halves 9 and 10.

Figure 2:
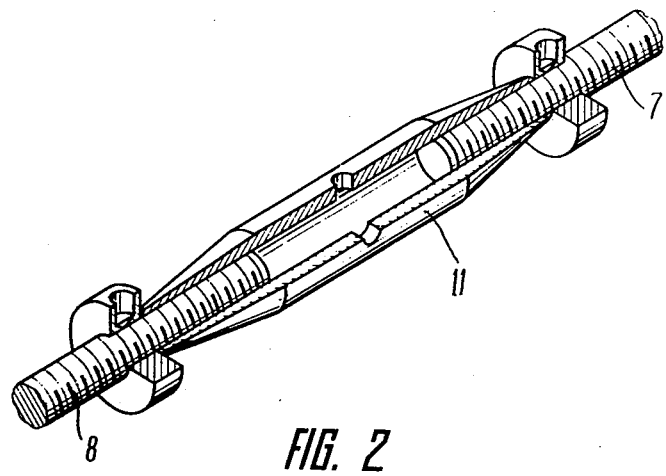
FIG. 2 is a partially sectional perspective view of a turnbuckle of the apparatus, in accordance with the invention.

The halves 7 and 8 of the yoke 4 have differently threaded portions on their ends for connection to each other through a sleeve 11 (FIGS. 1 and 2), thus forming a turnbuckle means. The halves 9 and 10 of the yoke 5 (FIG. 1) are identical and interconnected through threaded sleeve 12. The threaded sleeves 11 and 12 make it possible to adjust the size of the yokes 4 and 5, thereby changing the distance between the struts 2 and 3 secured in the yokes 4 and 5.

Longitudinal slots 13 in the yokes 4 and 5 provide for the struts 2 and 3 being also movable along the yokes 4 and 5.

Fastened by means of adjustable clamps 14 (FIG. 3) to the struts 2 and 3 are two stay rods 15, joined, in turn, with a thoracic belt 16, and two stay rods 17, joined to a pelvic belt 18. Thus, the clamps 14 form an adjustable connecting means for adjustably connecting the rods 15 and 17 to the strut means 2, 3.

The thoracic belt 16 and pelvic belt 18 are intended for securing the framework of the apparatus formed by the struts 2, 3 and the yokes 4 and 5 on the patient's trunk.

Two holes, their axes crossing at right angles, are made in the adjustable clamp 14 (FIGS. 1 and 3) for the strut 2 or 3 to pass through one of them and the stay rod 15 or 17 through the other, with the strut 2 or 3 and stay rod 15 or 17 touching one another.

The adjustable clamps 14 make it possible to adjust the position of the stay rods 15 and 17 in height on the struts 2 and 3, and also to adjust the length of the stay rods 15 and 17 between the struts 2 and 3 and the belts 16 and 18 (FIG. 1) and to adjust also the rotation of the stay rods 15 and 17. The stay rods 15 and 17 are fixed in position relative to the struts 2 and 3 by means of a set screw 19.

Figure 4:
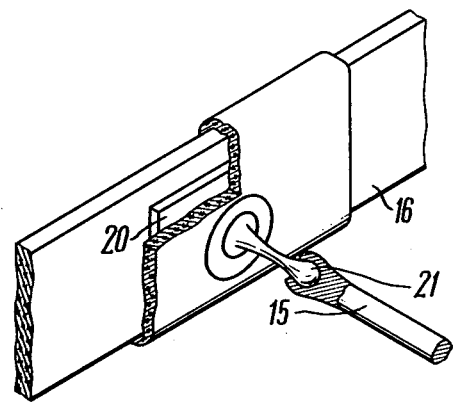
FIG. 4 shows the attachment of a stay rod to a belt of the apparatus, in accordance with the invention.

The stay rod 15 is hinged to the thoracic belt 16 (FIG. 4). For effecting this connection, attached to the thoracic belt 16 is a plate 20 with a ball-ended pin 21, which is grasped by a spherical socket on the stay rod 15. Thus, the structure forms a means for connecting the inner ends of the rods 15 to the belt 16 for movement in all directions with respect thereto. The stay rods 17 (FIG. 1) are connected in the same way with the pelvic belt 18.

Figure 5:
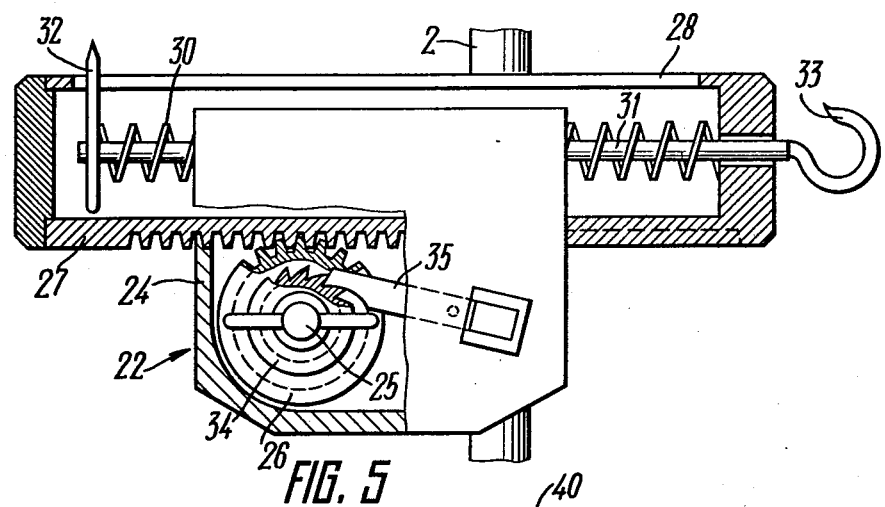
FIG. 5 shows a mechanism for the dosed tension of the flexible braces of the apparatus, in accordance with the invention.
Figure 6:
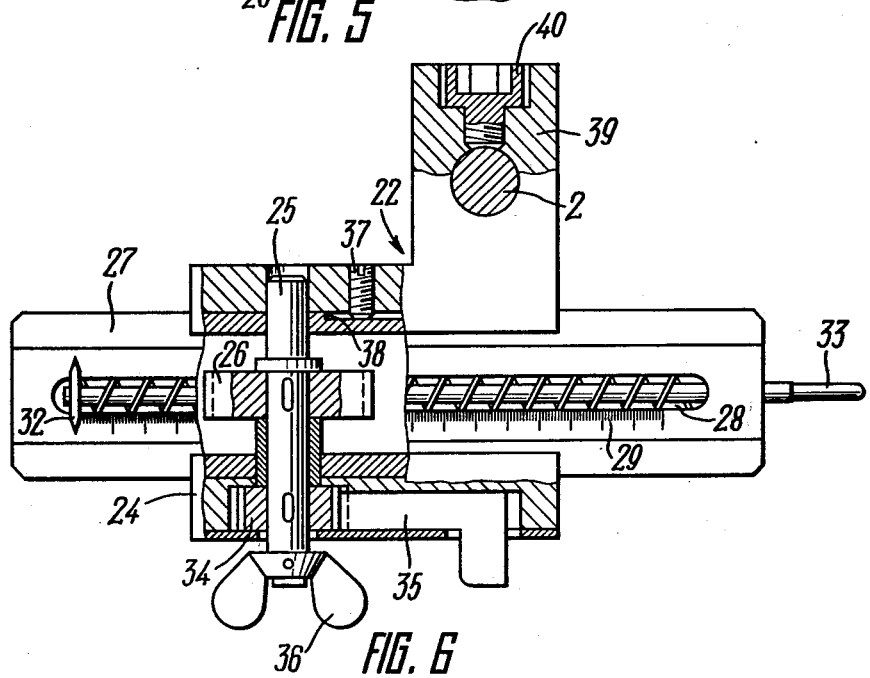
FIG. 6 is a top view of the mechanism of FIG. 5.

Also secured on the struts 2 and 3 are dynamometer means, formed by mechanisms 22, for the dosed tension of a flexible brace means formed by the flexible braces 23. The mechanism 22 is a rack-and-pinion one and comprises a body 24 (FIGS. 5 and 6) accommodating a shaft 25, set whereon is a pinion 26 engaged with a hollow rack sleeve 27, movable longitudinally. The teeth of the rack are made only on the one side of the rack sleeve 27 turned towards the pinion 26, while on the opposite side of the rack sleeve 27 there is a longitudinal through-slot 28, graduated on one side of which is a scale 29 (FIG. 6). Housed in the rack sleeve 27 is a dynamometer, formed by a compressed spring 30 (FIG. 5) with a rod 31 which has, on one end, a pointer 32 protruding through the slot 28 and serving as the indicator of tension. The other end of the rod 31 extending from the rack sleeve 27 has a hook 33 whereto the flexible brace 23 (FIG. 1) is fastened.

Also fitted on the shaft 25 (FIG. 6) is a ratchet wheel 34 which interacts with a catch pawl 35 of the ratchet, and a hand nut or handle 36. Screwed into the body 24 is a stop 37 interacting with a shoulder 38 of the rack sleeve 27, during its longitudinal travel, by limiting the length of that travel.

The body 24 of the mechanism 22 is provided with a lug 39 with a hole therein through which the strut 2 passes, and which is secured relative to the latter by a stop screw 40. Thus, this structure provides a connecting means for adjustably connecting the dynamometer means 22 to the strut means. Such mounting of the mechanisms 22 for the dosed tension of the flexible braces 23 (FIG. 1) allows the mechanisms 22 to be moved along the struts 2 and 3, and turned in the transversal plane about the struts 2 and 3.

Figure 7:
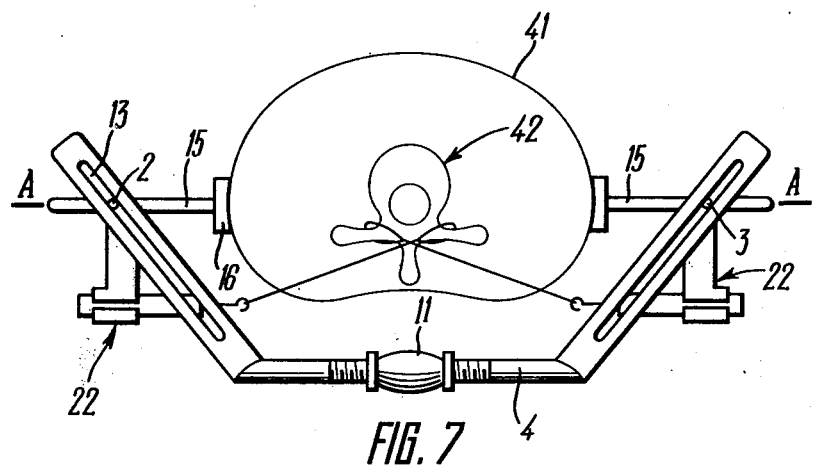
FIG. 7 is a schematic top view of the apparatus secured on a patient's trunk, in accordance with the invention.

The dimensions and outline of the yokes 4 and 5 of the apparatus are so selected as to encircle the patient's trunk 41 (FIG. 7) when applying the apparatus, enabling the struts 2 and 3 to be situated along both sides of the patient's trunk 41, approximately in plane A-A of the spinal column 42.

Figure 8:
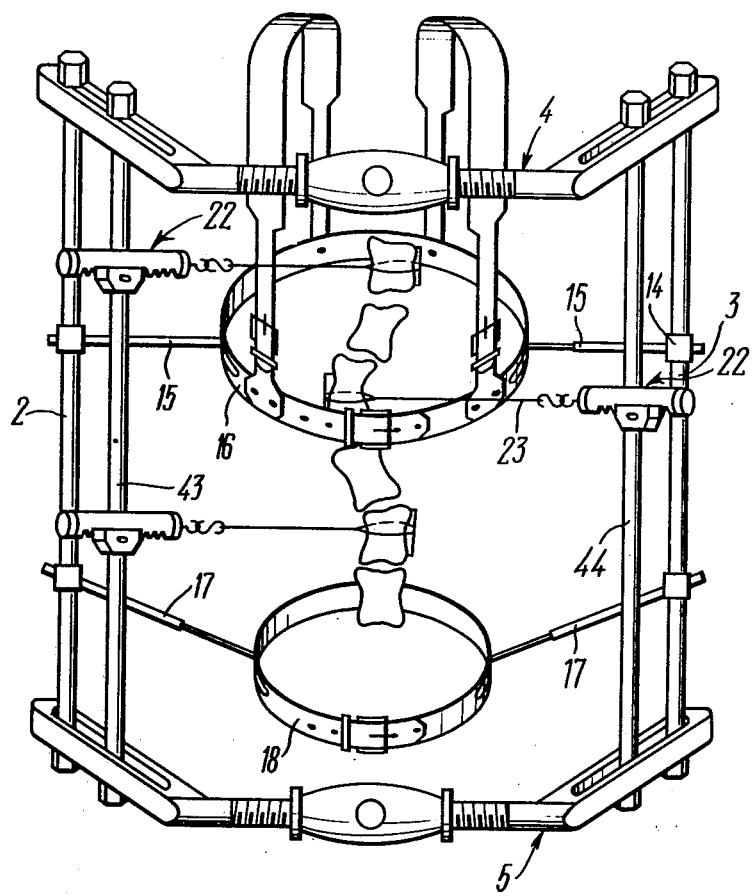
FIG. 8 shows an apparatus for the surgical treatment of scoliosis with two pairs of struts, in accordance with the invention.
Figure 9:
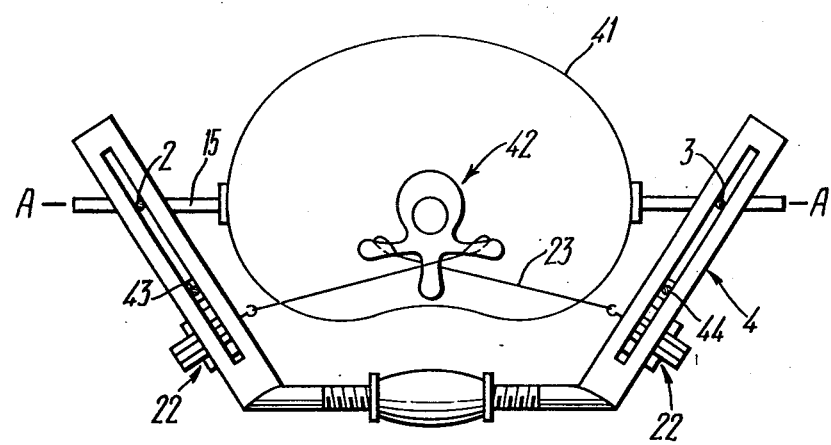
FIG. 9 is a schematic top view of the apparatus of FIG. 8 secured on the patient's trunk.
Figure 10:
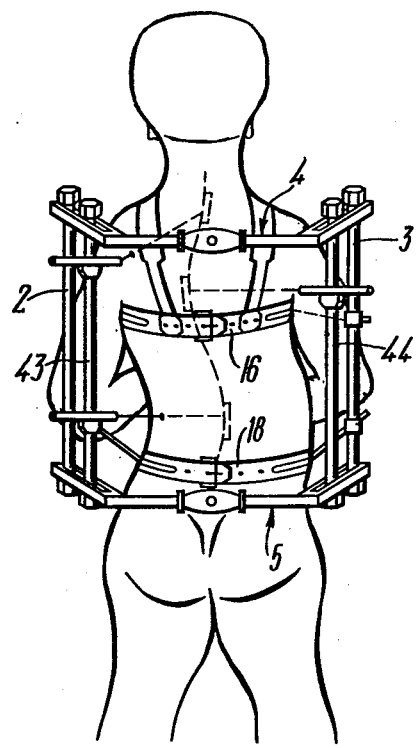
FIG. 10 shows the apparatus of FIG. 8 secured on the trunk of a patient.

The proposed apparatus for the surgical treatment of scoliosis may be fitted with a strut means including an additional pair of struts 43 and 44 (FIG. 8). In this case, to the struts 2 and 3 the stay rods 15 and 17 are secured, and to the struts 43 and 44, the mechanisms 22 for the dosed tension of the flexible braces 23. The struts 2 and 3, in this case, are situated along both sides of the patient's trunk 41 (FIG. 9) approximately in plane A—A of the spinal column 42, while the struts 43 and 44 are somewhat shifted along the yokes 4 and 5 (FIGS. 8 and 10) towards their tips. This allows, by moving the struts 43 and 44 with the mechanisms 22 (FIG. 9) secured thereon, to adjust in a wider range the angle of inclination of the flexible braces 23 to the patient's trunk 41 at the sites of their emergence from the trunk 41 and to prevent in this way sores of the patient's soft tissues and the cutting of the skin with the flexible braces 23.

The apparatus for the surgical treatment of scoliosis operates in the following way.

Before applying the apparatus, the flexible braces 23 are fastened to the spinal column. For this purpose, by longitudinal incision of the skin and soft tissues on the convex side of the maximum curvature of the scoliotic arch, a bed is formed on the vertebral arches along their spinous processes, five-six vertebrae long, according to the generally known methods. Placed on the bed is a preliminarily prepared autoplastic bone graft (FIGS. 11 and 12) taken from the shinbone. A Kapron (nylon) thread, which is the flexible brace 23, is drawn in a loop around the base of a transverse process 46 of one or two vertebrae situated at the apex of the curvation on the inner side of the main curvature. The ends of the thread are passed over the autoplastic graft 45, drawn between the spinous processes of the vertebrae to be brought out through the soft tissues and opening in the skin along the posterior axillary line. Sutures are placed on the wound.

By about 4 cm long incisions of the skin and soft tissues on the convex sides of the counter-curvations of the spinal column above and below the maximum curvation, transverse processes 47 and 48 (FIG. 11) of the vertebrae are exposed, and kapron threads are drawn, according to the method described.

Figure 13:
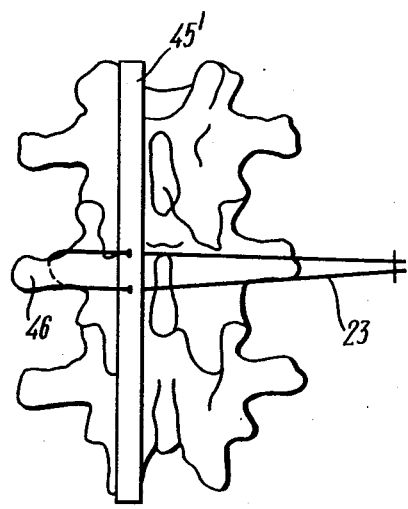
FIGS. 13, 14 and 15 show different methods of fastening a flexible brace of the apparatus to the transverse processes of vertebrae in accordance with the invention.
Figure 14:
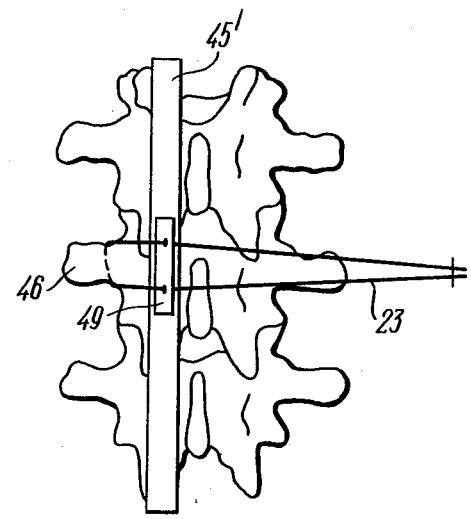

After engaging the thread hook with the transverse process 46 of the vertebra, the threads may be drawn not over the autoplastic bone graft 45', but, as shown in FIG 13, through two holes in the autoplastic bone graft 45'. For more reliable fixation of the thread loop, for example, in the thoracic region of the spinal column, it is advisable to place on the autoplastic bone graft 45' a heteroplastic bone graft plate 49 (FIG. 14), 2.5 × 1 × 0.2 cm is size. In this case, the ends of the thread are drawn through holes in the two bone grafts.

Figure 15:
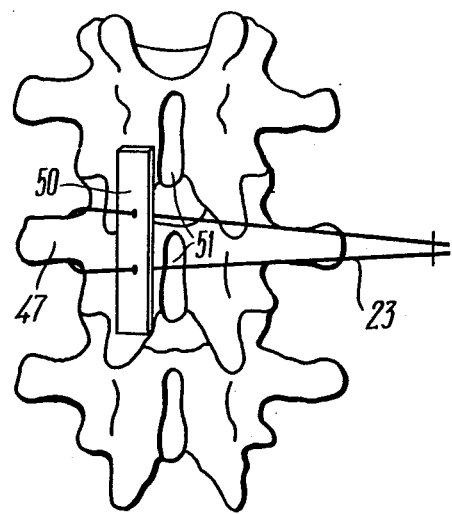

It is advisable to secure the point of opposite tension (contraextension) in the upper thoracic region with a heteroplastic bone graft plate 50 (FIG. 15) of the above indicated size, placing it at spinous processes 51 of the vertebrae.

Figure 16:
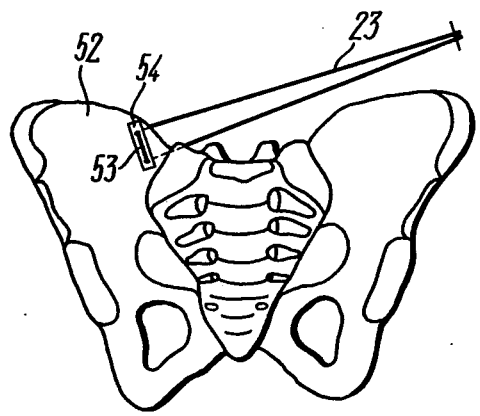
FIG. 16 shows the fastening of a flexible brace of the apparatus to the iliac bone, in accordance with the invention.

In the case of unilateral C-shaped curvation of the entire spinal column, and also in S-shaped scolioses with predominantly lumbar curvation, it is advisable to select the lower point of contraextension on the posterior-superior spine of the iliac bone 52 (FIG. 16) and place a plate 54 of a heteroplastic bone graft under a loop 53 of the flexible brace 23.

In each case, the plate of the heteroplastic bone graft plays the role of a safety washer protecting bone tissues from being cut by the kapron thread.

Openings in the skin at the points where the threads are brought out, and also the skin wounds are isolated with alcohol-moistened napkins and zinc-gelatin paste.

For mounting the apparatus, the thoracic belt 16 (FIG. 10) and the pelvic belt 18 are fastened on the patient with the buckles of the belts 16 and 18 situated at the patient's back.

Then, by moving the struts 2 and 3 in the slots 13 (FIG. 1) of the yokes 4 and 5, and also by rotating the threaded sleeves 11 and 12, the frame work of the apparatus is adjusted to the sizes of the lumbar and thoracic parts of the patient's trunk and is secured in that position by means of the nuts 6.

Figure 3:
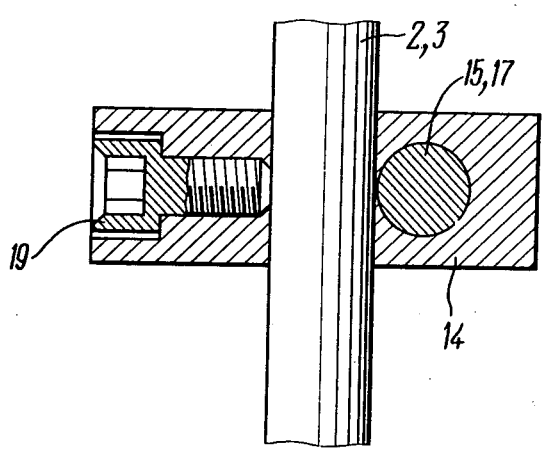
FIG. 3 is a section view of an adjustable clamp of the apparatus, in accordance with the invention.

By moving the adjustable clamps 14 and the stay rods 15 and 17, the latter are set in a position whereby the plates 20 (FIG. 4) slightly press through the belts 16 and 18 (FIG. 1) against the patient's body, and this position of the stay rods 15 and 17 is secured with the screws 19 (FIG. 3).

The mechanisms 22 (FIG. 1) for the dosed tension of the flexible braces 23 are set approximately against the sites where the flexible braces 23 emerge from the patient's trunk and are secured in this position. The ends of the flexible braces 23, brought out through the soft tissues and skin of the back, are fastened to the hooks 33 (FIG. 5) of the mechanisms 22. For fastening the flexible braces to the hooks 33 and their preliminary tightening the catch pawl 35 is released, by rotating the hand nut 36 (FIG. 6) clockwise the rack sleeve 27 is moved to the right and the flexible brace is tied to it.

In order to tighten the flexible brace the hand nut 36 is rotated counterclockwise, thereby moving the rack sleeve 27 to the left, as indicated in the drawing. Here the pointer 32 indicates the force of the tension.

By unwinding the threaded sleeves 11 and 12 (FIG. 1) the extension force applied to the main scoliotic curvature is brought up to 8–10 kg, its magnitude being checked by the dynamometer readings.

During the two weeks following the application of the apparatus, the dynamometer readings on the mechanisms 22 gradually diminish due to the correction of the scoliosis. After two weeks, a control X-ray of the spinal column is taken. If the X-ray picture indicates full correction of scoliosis, the extension force is left within 3–4 kg to support the corrected position and to ensure that the autoplastic graft takes and spondylodesis occurs within the subsequent 2–2.5 months.

If the control X-ray shows that the correction is insufficient, the extension force is increased to 8–10 kg, and this tension is maintained till the full correction of the scoliosis.

The term of treatment (2.5–3 months) being over, the apparatus is removed. To this end, one string of the loop of the flexible brace 23 is cut at the skin opening and the flexible brace is pulled out by the other string.

Then, the buckles of the belts 16 and 18 are undone and the apparatus is taken off.

What is claimed is:

1. Apparatus for the surgical treatment of scoliosis, comprising: belt means to be strapped onto a patient's body, frame means to be situated at the exterior of the patient's body adjacent said belt means, said frame means including upper and lower yokes and upright strut means extending vertically between and fixed with said yokes, said strut means including at least one pair of upright struts for extending along both sides of the patient's trunk approximately in alignment with the spinal column, a plurality of stay rods respectively having inner ends operatively connected with said belt means and extending from said belt means outwardly toward the region of said strut means, adjustable connecting means adjustably connecting said stay rods with said strut means, flexible brace means to be secured to selected vertebrae while extending therefrom to the exterior of the patient's body, dynamometer means situated at the exterior of the patient's body and operatively connected with said flexible brace means for applying a predetermined tension thereto, and adjustable connecting means adjustably connecting said dynamometer means to said strut means, so that through said flexible brace means a corrective force can be exerted on the vertebrae.

2. The combination of claim 1 and wherein each yoke includes a pair of yoke halves, and turnbuckle means interconnecting said halves of each yoke for adjusting the distance between the struts at the sides of the patient's trunk.

3. The combination of claim 1 and wherein a connecting means turnably connects said inner ends of said stay rods to said belt means for turning movement in all directions with respect to said belt means.

4. The combination of claim 1 wherein said yokes include means connecting said struts thereto for movement along said yokes for adjusting the distance between said struts.

5. The combination of claim 1 and wherein said dynamometer means includes a spring means operatively connected with said flexible brace means, rack-and-pinion means operatively connected with said spring means for adjusting the force thereof, and ratchet means operatively connected with said rack-and-pinion means for maintaining the latter in a position acting on said spring means to provide a given tension in said flexible brace means.

6. The combination of claim 1 and wherein said yokes include a means for connecting said yokes to said struts for movement therealong for adjusting the distance between said yokes.

7. The combination of claim 1 and wherein said strut means includes four upright struts extending between and operatively connected with said yokes, said struts which are situated along the sides of the patient's trunk being operatively connected with said stay rods, while the remaining struts are operatively connected through said dynamometer means with said flexible brace means.

8. The combination of claim 1 and wherein said flexible brace means is in the form of a thread.

9. The combination of claim 8 and wherein said thread is made of nylon.

10. The combination of claim 1 and wherein an autoplastic bone graft is applied to the vertebrae and serves to guide the flexible brace means.

11. The combination of claim 10 and wherein the flexible brace means is in the form of a thread extending in part around the autoplastic bone graft.

12. The combination of claim 10 and wherein the flexible brace means is in the form of a thread and said autoplastic bone graft is formed with at least one opening through which the thread extends.

* * * * *